United States Patent

Beaty et al.

[11] Patent Number: 6,055,054
[45] Date of Patent: *Apr. 25, 2000

[54] THREE DIMENSIONAL INSPECTION SYSTEM

[76] Inventors: Elwin M. Beaty, 13529 Arthur St., Minnetonka, Minn. 55305; David P. Mork, 14605 34th Ave. North, No. 209, Plymouth, Minn. 55447

[*] Notice: This patent is subject to a terminal disclaimer.

[21] Appl. No.: 08/850,473

[22] Filed: May 5, 1997

[51] Int. Cl.⁷ .............................. G01B 11/24; G06K 9/00
[52] U.S. Cl. ...................... 356/376; 356/394; 356/237.1; 382/146; 348/126
[58] Field of Search ..................... 356/237, 394, 356/375, 376; 348/126, 87; 382/153, 291, 145, 146, 147, 149, 154

[56] References Cited

U.S. PATENT DOCUMENTS

| | | |
|---|---|---|
| 4,521,807 | 6/1985 | Werson . |
| 4,638,471 | 1/1987 | van Rosmalen . |
| 4,677,473 | 6/1987 | Kazunari et al. . |
| 4,731,855 | 3/1988 | Suda et al. . |
| 4,825,394 | 4/1989 | Beamish et al. . |
| 4,886,958 | 12/1989 | Merryman et al. . |
| 4,943,722 | 7/1990 | Breton et al. . |
| 5,058,178 | 10/1991 | Ray . |
| 5,095,447 | 3/1992 | Manns et al. . |
| 5,113,581 | 5/1992 | Hidese ...................................... 29/840 |
| 5,133,601 | 7/1992 | Cohen et al. . |
| 5,140,643 | 8/1992 | Izumi et al. ................................ 382/8 |
| 5,173,796 | 12/1992 | Palm et al. . |
| 5,204,734 | 4/1993 | Cohen et al. . |
| 5,245,671 | 9/1993 | Kobayashi et al. . |
| 5,276,546 | 1/1994 | Palm et al. . |
| 5,307,149 | 4/1994 | Palm et al. . |
| 5,355,221 | 10/1994 | Cohen et al. . |
| 5,420,689 | 5/1995 | Sin . |
| 5,420,691 | 5/1995 | Kawaguchi .............................. 356/375 |
| 5,430,548 | 7/1995 | Hiroi et al. . |
| 5,452,080 | 9/1995 | Tomiya ................................... 356/237 |
| 5,465,152 | 11/1995 | Bilodeau et al. . |
| 5,513,276 | 4/1996 | Theodoracatos ........................ 356/376 |
| 5,546,189 | 8/1996 | Svetkoff et al. . |
| 5,550,763 | 8/1996 | Michael et al. . |
| 5,563,702 | 10/1996 | Emery et al. . |
| 5,563,703 | 10/1996 | Lebeau et al. .......................... 356/237 |
| 5,574,668 | 11/1996 | Beaty . |
| 5,574,801 | 11/1996 | Collet-Beillon . |
| 5,581,632 | 12/1996 | Koljonen . |
| 5,592,562 | 1/1997 | Rooks . |
| 5,600,150 | 2/1997 | Stern et al. . |
| 5,617,209 | 4/1997 | Svetkoff et al. . |
| 5,621,530 | 4/1997 | Marrable, Jr. . |
| 5,648,853 | 7/1997 | Stern et al. . |
| 5,652,658 | 7/1997 | Jackson et al. . |
| 5,654,800 | 8/1997 | Svetkoff et al. . |
| 5,692,070 | 11/1997 | Kobayashi . |

(List continued on next page.)

FOREIGN PATENT DOCUMENTS

| | | |
|---|---|---|
| WO9112489 | 8/1991 | WIPO . |
| WO9207250 | 4/1992 | WIPO . |

OTHER PUBLICATIONS

CI-8250, The Complete High-Speed Inspection System, ICOS' Products, 6 pages.

*Primary Examiner*—Hoa Q. Pham
*Attorney, Agent, or Firm*—Moffa & Sun, P.A.

[57] ABSTRACT

A part inspection and calibration method for the inspection of printed circuit boards and integrated circuits includes a camera to image a precision pattern mask deposited on a transparent reticle. Small parts are placed on or above the transparent reticle to be inspected. An overhead mirror or prism reflects a side view of the part under inspection to the camera. The scene of the part is triangulated and the dimensions of the system can thus be calibrated. A precise reticle mask with dot patterns gives an additional set of information needed for calibration. By imagining more than one dot pattern the missing state values can be resolved using an iterative trigonometric solution. The system optics are designed to focus images for all perspectives without the need for an additional focusing element.

27 Claims, 11 Drawing Sheets

U.S. PATENT DOCUMENTS

| | | |
|---|---|---|
| 5,734,475 | 3/1998 | Pai . |
| 5,801,966 | 9/1998 | Ohashi . |
| 5,812,268 | 9/1998 | Svetkoff et al. . |
| 5,815,275 | 9/1998 | Svetkoff et al. . |
| 5,818,061 | 10/1998 | Stern et al. . |
| 5,828,449 | 10/1998 | King et al. . |
| 5,859,698 | 1/1999 | Chau et al. . |
| 5,859,924 | 1/1999 | Liu et al. . |
| 5,870,489 | 2/1999 | Yamazaki et al. . |

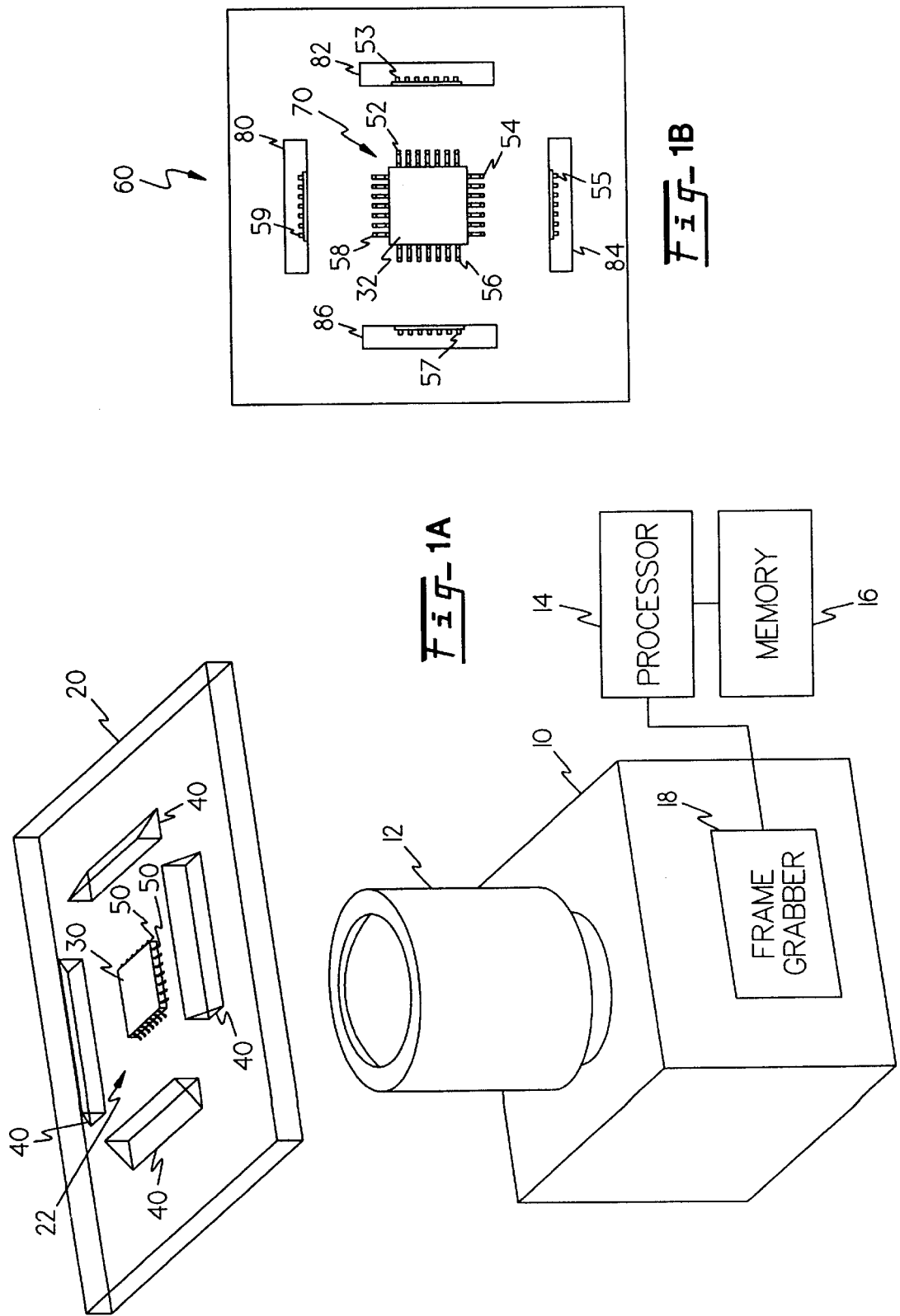

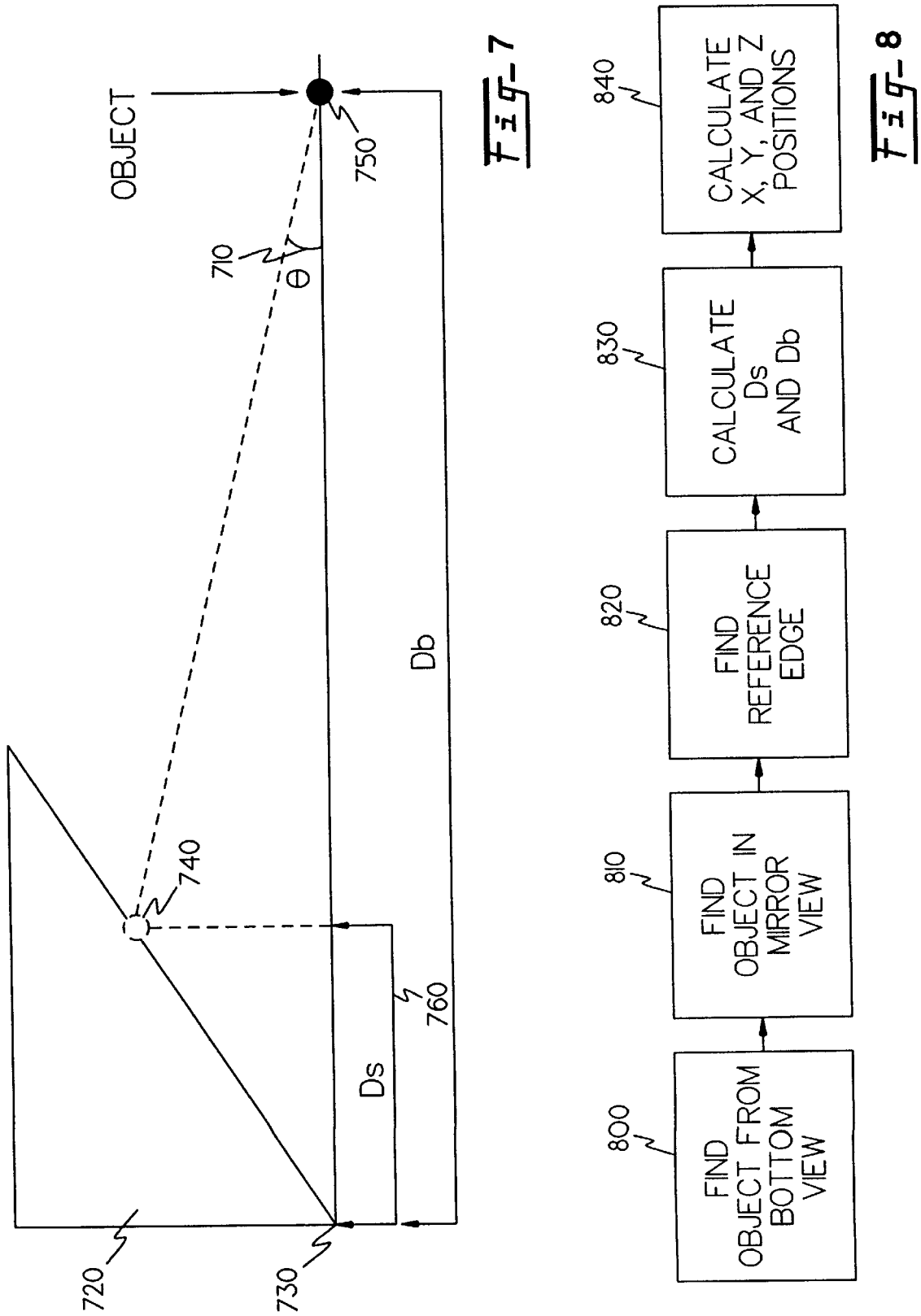

US 6,055,054

THREE DIMENSIONAL INSPECTION SYSTEM

This invention relates to a method and apparatus for three dimensional inspection and, more particularly, a method and apparatus for three dimensional inspection of electrical component leads using a single axial camera and a single image.

BACKGROUND OF THE INVENTION

Prior art three dimensional inspection systems have involved multiple access mirrors and multiple cameras or a single camera and multiple images. These systems have been used to inspect printed circuit boards, integrated circuits and other small parts. The prior art requires a multiple number of images to accomplish the three dimensional inspections. Traditional prior art methods utilize a triangulation method that requires multiple images. Multiple images increase the cost of prior art solutions as well as the complexity and the time needed for inspection.

Prior art solutions do not include a method or apparatus for providing three dimensional inspections of a part having leads from a single image. Using a single image for three dimensional systems provides a speed and cost benefit. It is therefore a motivation of the invention to provide a three dimensional scanning system for a part having leads where the scanning system requires only one image of the part being taken.

Other scanning systems are disclosed in U.S. Pat. No. 5,173,796, issued Dec. 22, 1992 to Palm et al., entitled "THREE DIMENSIONAL SCANNING SYSTEM" and U.S. Pat. No. 5,276,546, issued Jan. 4, 1994 to Palm et al., entitled "THREE DIMENSIONAL SCANNING SYSTEM" the disclosures of which are incorporated herein, in their entirety, by the foregoing references thereto.

SUMMARY OF THE INVENTION

The invention provides a method and apparatus for three dimensional inspection of objects having electronic leads. An inspection system includes a transparent reticle for receiving a part for inspection on a central portion of the reticle. Optical elements are located around the central portion of the reticle to provide side views of the part to a single axial camera located below the reticle. The camera receives an image including a bottom view and side views. The reticle further provides a common reference point. A processor locates the position of a part feature in three dimensions using the relationship of the part feature to the common reference point. The processor calibrates the inspection system by imaging a precisely defined object such as a reticle mask to provide a set of dimensional data that is invariate over the system parameters. The calibration method provides a set of state equations. The need for a focusing element is eliminated through the choice of optics and the relative placement of the overhead mirrors or prisms with respect to the object to be inspected. The difference in optical path lengths between the bottom view and the overhead views are less than the depth of focus. Because only a single image is needed to provide the three dimensional analysis, the inspection system provides a cost effective, repeatable and high speed analysis.

The invention also provides a method for three dimensional inspection of electronic leads from a single image. The method starts by providing a transparent reticle having a top surface. The method then places a part having electronic leads for inspection on a central portion of the top surface of the transparent reticle. The method then provides fixed optical elements for providing a side perspective of the part. The method then provides a camera located beneath the transparent reticle to receive an image of the part and the additional perspective provided by the fixed optical elements wherein the camera provides image data. The method then processes the image data with a computer to provide a three dimensional analysis of the part.

The invention also provides a method to calibrate the computer using a reticle mask. In one embodiment the invention calibrates the computer by calibration of the bottom view by the following steps. The invention first locates the calibration dots on the reticle mask visible directly from the bottom view. The method then determines the location and size of each dot. The method then stores the location and size of each dot in memory. The method then determines the state values for the bottom calibration by comparing the location and size of each dot with the known values and then stores the state values in memory.

The invention further provides for calibration of the computer by calibration of a side view by the following steps. First the method of the invention locates the calibration dots visible in each of the fixed optical elements. The method then locates a reference edge. The method then calculates a distance from the reference edge to each dot in the side view image and the bottom view image. The method then determines state values for the fixed optical elements from known values and stores the state values in memory.

The invention also provides three dimensional inspection of an object having electronic leads from a single image. The method first waits for an inspection signal. Then the method acquires an image of the object including a bottom view and a side view. The method then processes the image to find a rotation, x placement and y placement of the object. Then the method locates the electronic leads of the object in the bottom view. The method then locates the electronic leads of the object in the side view and determines a reference point for each lead. The method then converts pixel values to world values. The method then converts word values to part values. The method then converts part values to measurement values, wherein the measurement values are determined by comparing the calculated part values to predetermined part values. Finally the method provides a part result based on the measurement values and predetermined tolerance values.

In one embodiment the part result comprises a result selected from the list consisting of: a pass result, a fail result and a rework result.

In another embodiment the predetermined tolerance values further comprise pass tolerance values and fail tolerance values.

In one embodiment the part result comprises a pass result if the measurement values are less than or equal to the pass tolerance values, a fail result if the measurement values exceed the fail tolerance values and a rework result otherwise.

In one embodiment the part may be removed after the camera acquires the image and a new part placed on the transparent reticle while the part result is calculated.

BRIEF DESCRIPTION OF THE DRAWINGS

To illustrate this invention, a preferred embodiment will be described herein with reference to the accompanying drawings.

FIG. 1A shows the apparatus of the invention for part inspection and calibration.

FIG. 1B shows an example image acquired by the system.

FIG. 7 shows a method for calibration of the optical elements.

FIG. 8 shows a flow chart of a method of the invention for determining three dimensional location.

DETAILED DESCRIPTION OF THE PREFERRED EMBODIMENT

Figure 1C:
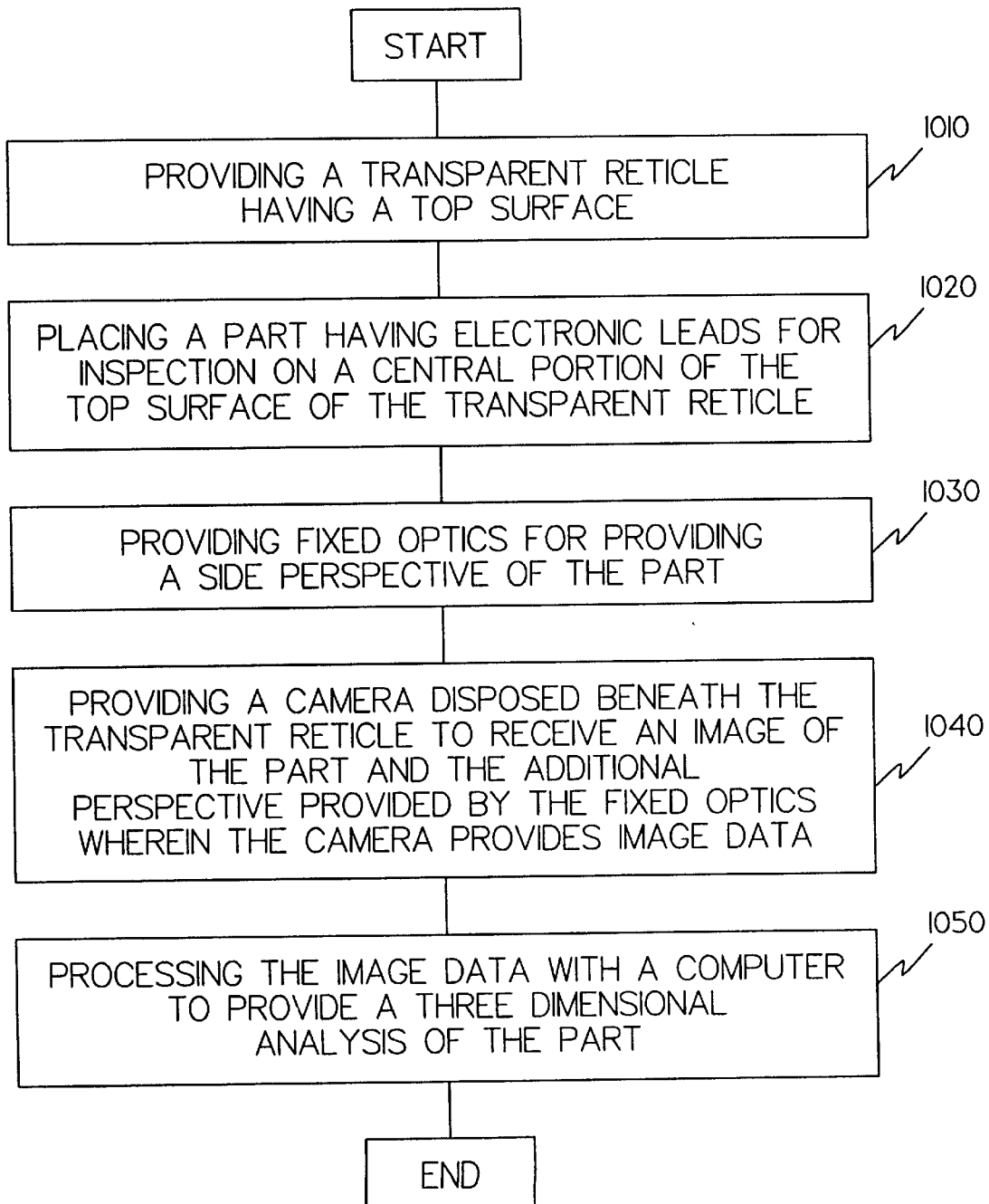
FIG. 1C shows a method for three dimensional inspection of electronic leads from a single image.

In one embodiment of the invention, the method and apparatus disclosed herein is a method and apparatus for three dimensional inspection of objects having electronic leads.

FIG. 1A shows the apparatus of the invention for three dimensional inspection. The apparatus includes a camera 10 with a lens 12 and a reticle 20. The reticle 20 includes a central region 22 for receiving a part 30 having a lead 50 for imaging by the camera. The camera 10 is located below the central region 22 of the reticle 20 to receive an image of the part 30. The reticle 20 includes optical elements 40 to provide additional perspectives of the part 30. The optical elements 40 are attached to the reticle and are located around the central region 22 to provide multiple side views of the part 30 to the camera 10. In one embodiment of the invention, the optical elements 40 may comprise prisms. In an alternate embodiment of the invention, the optical elements 40 may comprise mirrors.

The camera 10 is located to receive the image of part 30 and the additional perspectives provided by the optical elements 40. The camera 10 includes a frame grabber board 18 to capture the image. The optics of the camera 10 have a depth of focus encompassing the optical paths of the bottom view from the reticle 20 and the side views provided from the optical elements 40. The camera 10 provides an image data output to a processor 14 to perform a three dimensional inspection as described in conjunction with FIGS. 2A and 2B. The processor 14 may store the image in a memory 16.

FIG. 1B shows an example image acquired by the system shown in FIG. 1A. The image 60 obtained by the camera 10 includes a bottom view 70 obtained by the view through the reticle 20. The bottom view 70 shows an image of the part 32 and images of the leads 52, 54, 56, 58. The image 60 further includes four side images 80, 82, 84, 86 obtained by the view through reticle 20 and reflected off the optical elements 40. The side images 80, 82, 84, 86 show a respective side image of the part 32 and the corresponding leads 53, 55, 57, 59. For example, lead 53 in side view 82 corresponds to lead 52 in bottom view 70, lead 55 in side view 84 corresponds to lead 54 in bottom view 70, and so on. As will be appreciated by those skilled in the art, the invention will work with any number of side images. For example, one image may be used for inspecting a single row of leads. Two images may be used for two rows of leads.

Refer now to FIG. 1C which shows a method for three dimensional inspection of electronic leads from a single image. The method starts by providing a transparent reticle having a top surface in step 1010. The method then places a part having electronic leads for inspection on a central portion of the top surface of the transparent reticle in step 1020. The method then provides fixed optical elements for providing a side perspective of the part in step 1030. The method then provides a camera located beneath the transparent reticle to receive an image of the part and the additional perspective provided by the fixed optical elements wherein the camera provides image data in step 1040. The method then processes the image data with a computer to provide a three dimensional analysis of the part in step 1050.

Figure 2A:
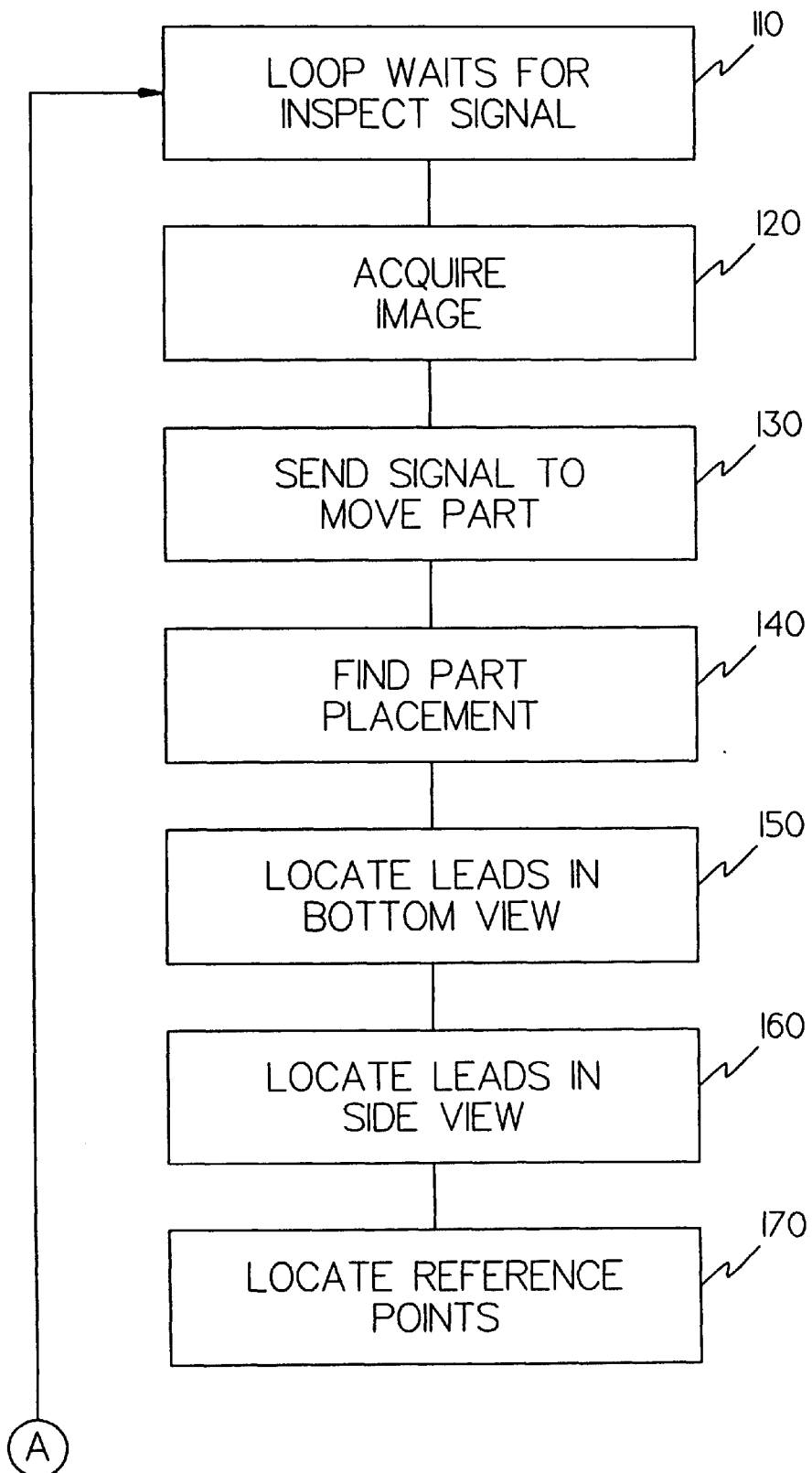
FIGS. 2A and 2B show a flow diagram of the three dimensional inspection loop of the invention.
Figure 2B:
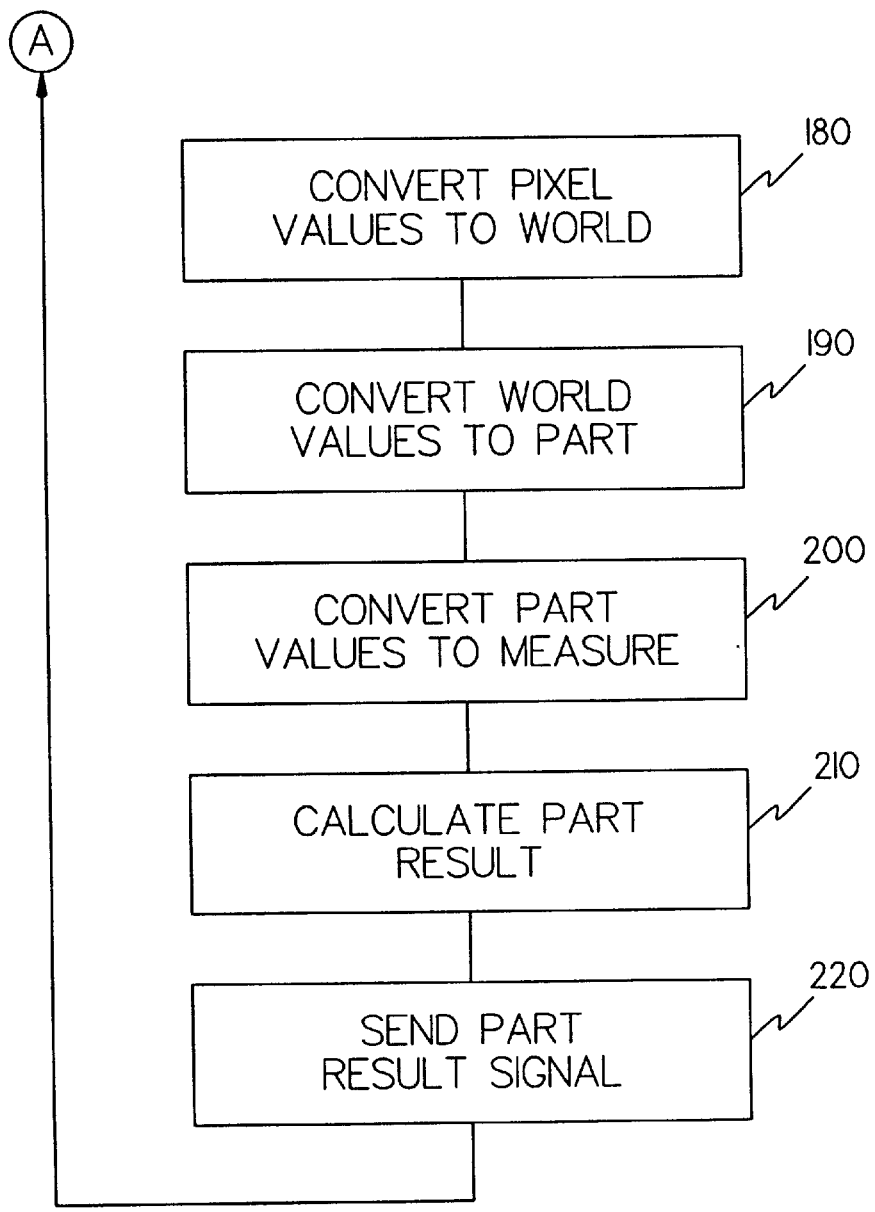

FIGS. 2A and 2B show a flow diagram of the three dimensional inspection loop of the invention. The process begins in step 110 by waiting for an inspection signal. When the signal changes state, the system initiates the inspection. The processor sends a command to a frame grabber board 18 to acquire an image of a part having leads from the camera in step 110. In step 120, the camera 10 captures an image comprising pixel values and the processor stores the image in memory. The image comprises information from both a bottom view of the part and a number of side views as shown in FIG. 1B.

Figure 9A:
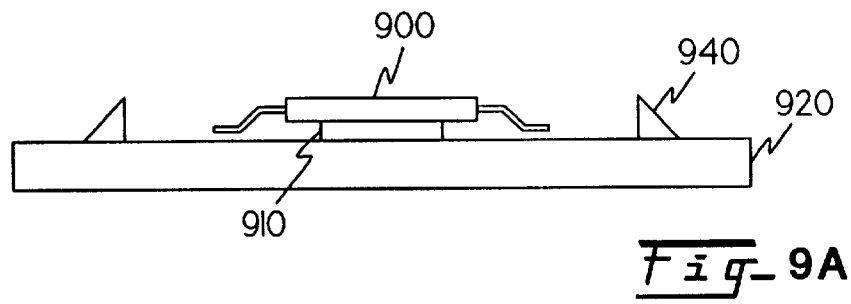
FIGS. 9A, 9B, 9C and 9D show alternate embodiments of the part holder and optical elements of the invention.
Figure 9B:
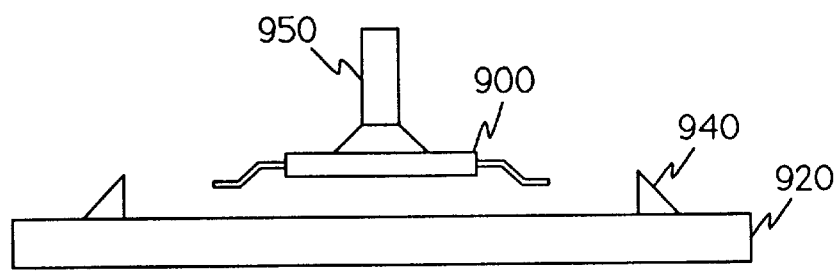
Figure 9C:
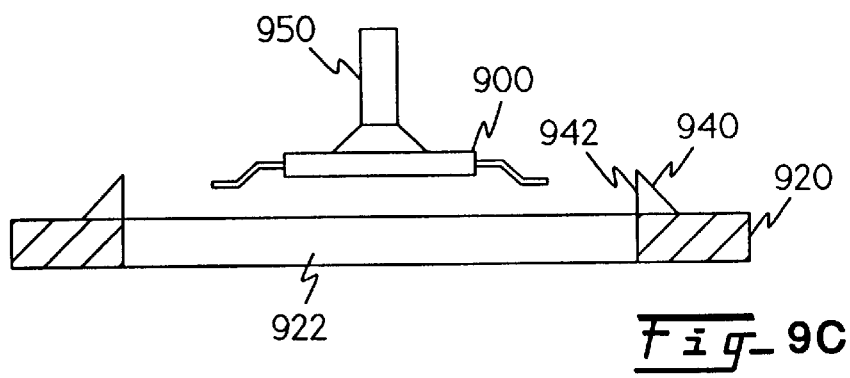
Figure 9D:
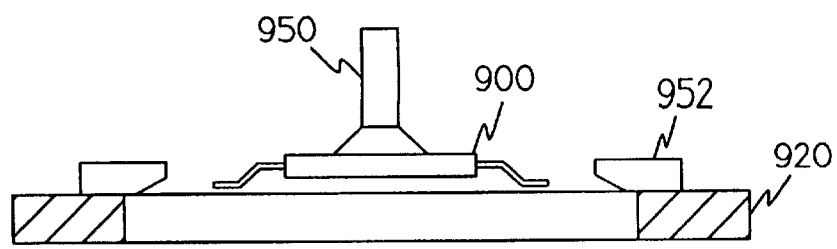

In step 130, the inspection system sends a signal to a part handler shown in FIGS. 9B, 9C and 9D that the part may be moved off the inspection reticle and that the next part may be put into place. The handler may proceed with part placement while the inspection system processes the stored image data.

Figure 4:
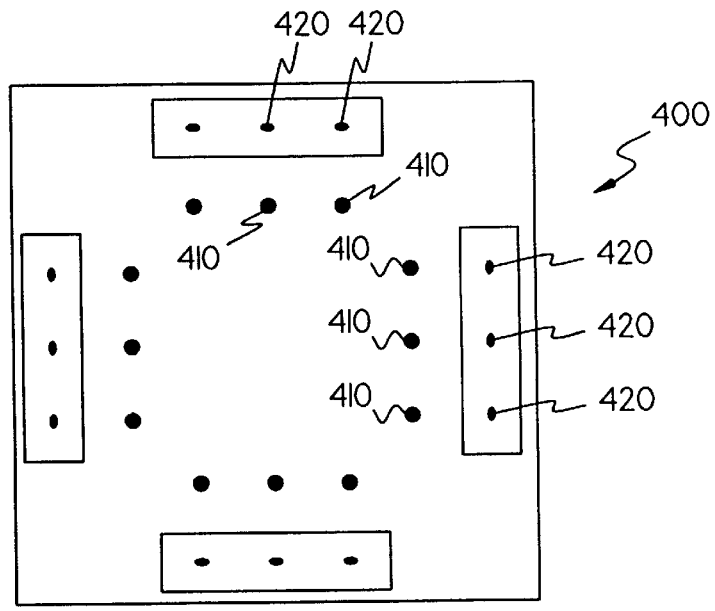
FIG. 4 shows one embodiment of a calibration dot pattern as viewed by a camera with four side optical elements.

The inspection system processes the pixel values of the stored image in step 140 to find a rotation, X placement, and Y placement of the part relative to a center point found during calibration of the inspection system using the reticle mask shown in FIG. 4. The processor determines these placement values finding points on four sides of the body of the part. In step 150, the processor employs a part definition file that contains measurement values for an ideal part. By using the measurement values from the part definition file and the placement values determined in step 140, the processor calculates an expected position for each lead of the part for the bottom view portion of the image. The processor employs a search procedure on the image data to locate the position of the lead closest to the expected position in the bottom view. The processor then determines the lead's X and Y position in pixel values by finding edges on three sides of each lead with a sub-pixel image processing method as shown in FIGS. 10A–10D.

Figure 6:
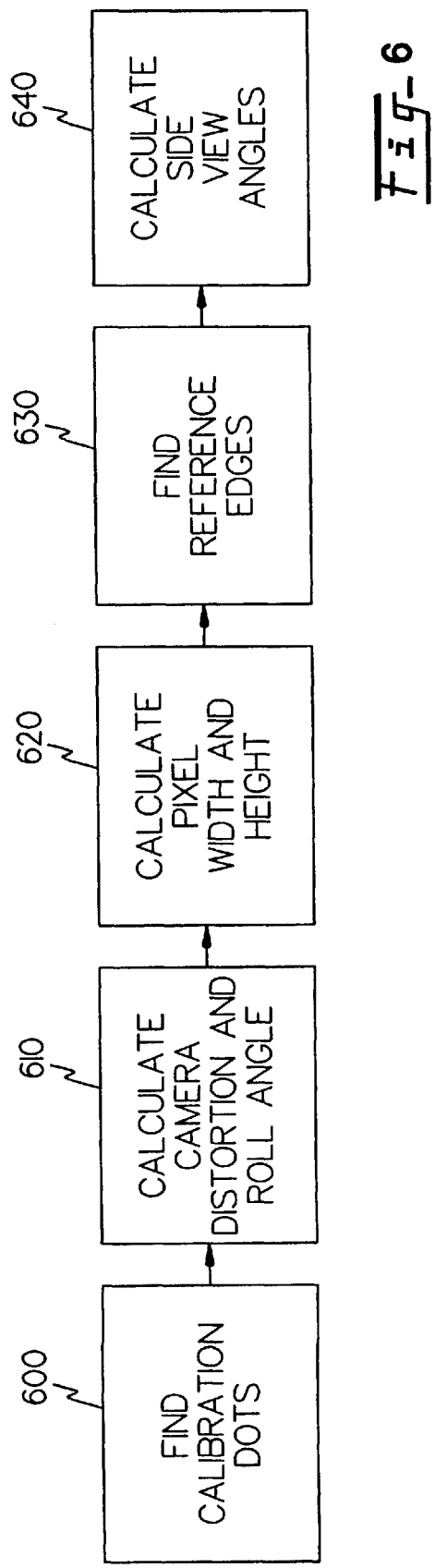
FIG. 6 shows a flow chart of a method of the invention used for system calibration.

The processor proceeds in step 160 to calculate an expected position of each lead in the side view of the image using the known position of the side view as determined during a calibration procedure as described in FIG. 6, and the position of the lead found in the bottom view. The processor employs a sub-pixel procedure to determine the Z position of the lead in pixel values as described in greater detail in conjunction with FIG. 3A.

After the processor locates the leads, the inspection loop flows to step 170 to determine a reference edge for each lead.

The processor determines a closest reference edge for each lead found in the side view. In one embodiment, the juncture of the optical elements with the reticle may serve as a reference edge. In an alternate embodiment, a reference edge may be inscribed on the transparent reticle. In another alternate embodiment, a virtual line of pixels may define the reference edge. The processor converts pixel values to world locations for each lead in step 180 by using the pixel values and parameters determined during calibration. The world locations represent physical locations of the leads in relation to the reference edge. The processor measures $D_S$ and $D_B$ dimensions and computes the Z dimension for each lead as further described in FIGS. 3A and 3B.

The processor then converts the world values to part values using the calculated part rotation, X placement, and Y placement in step 190 to define coordinates for the ideal part. The part values represent physical dimensions of the leads, such as lead length and lead width.

In step 200, these part values are compared to the ideal part values defined in the part file to calculate the deviation of each lead in three dimensions from the ideal location. In one example embodiment of the invention, the deviation values may include: tip offset, skew, bent lead, width and coplanarity. The processor compares these deviation values to predetermined thresholds with respect to the ideal part as defined in the part file in step 210 to provide an electronic lead inspection result. In one embodiment, the predetermined tolerance values include pass tolerance values and fail tolerance values from industry standards. If the measurement values are less than or equal to the pass tolerance values, the processor assigns a pass result for the part. If the measurement values exceed the fail tolerance values, the processor assigns a fail result for the part. If the measurement values are greater than the pass tolerance, but less than or equal to the fail tolerance, the processor designates the part to be reworked. The processor reports the inspection result for the part in step 220, completing part inspection. The process then returns to step 110 to await the next inspection signal.

Figure 3A:
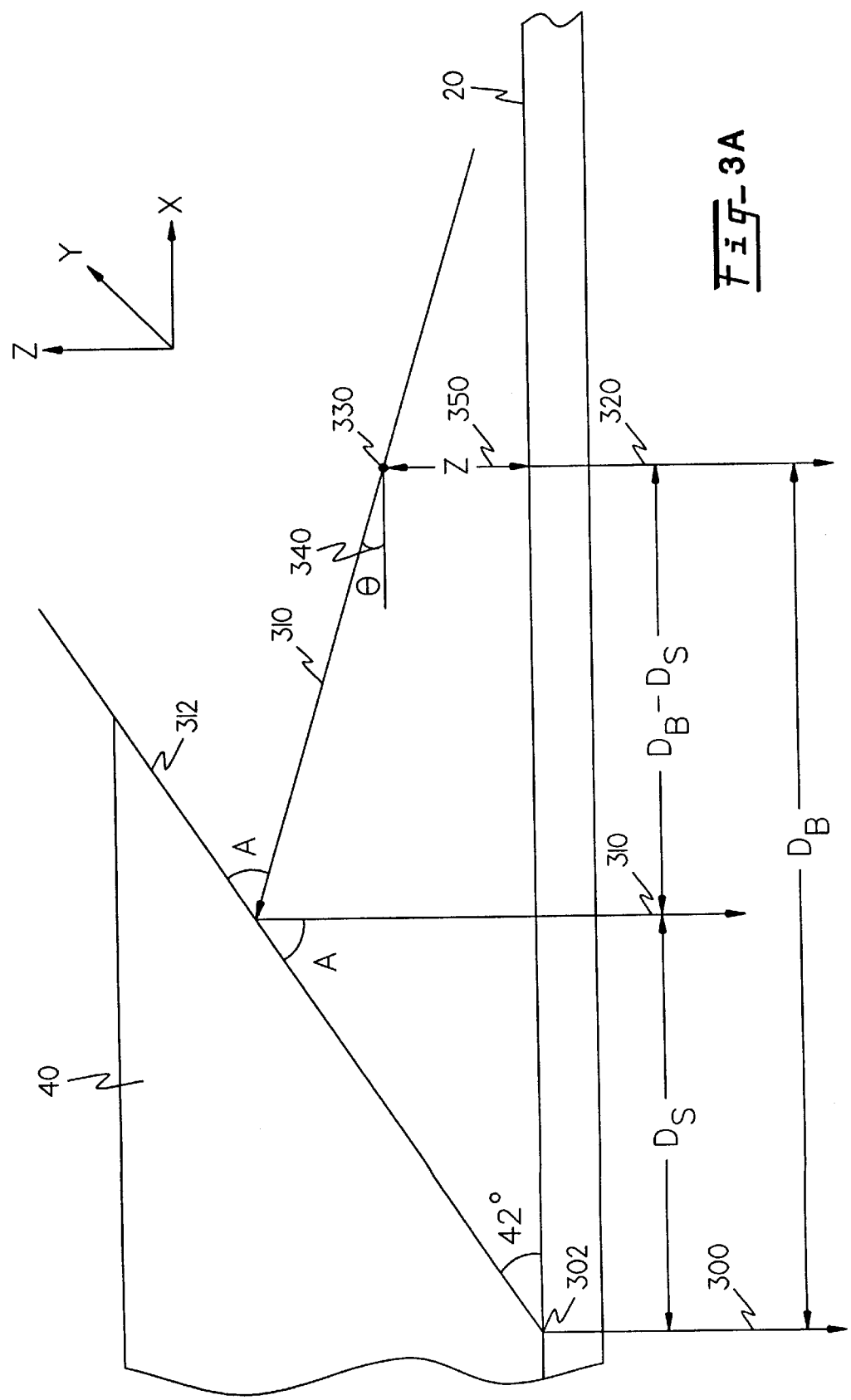
FIG. 3A shows one method of the invention used to locate an object in three dimensions.

FIG. 3A shows one method of the invention used to provide a three dimensional location of an object. Using parameters determined from the calibration procedure as shown in FIG. 6 and a single image, the processor computes a three dimensional location. The processor locates a reference line on the plane of the reticle 20 formed by the juncture of the optical element 40 with the plane of the reticle 20. Ray 300 shows the optical path from reference edge 302 to the camera 10. Rays 300, 310 and 320 are parallel with an axis of the camera 10. The processor measures a distance $D_S$ as the distance between the reference edge 302 and the reflected image of the object 330 of the reflective face 312 of the optical element 40 as shown by optical path 310. In one example embodiment, the angle of the reflective face 312 and the reticle 20 is 42°. One skilled in the art will realize that any angle may be used that will provide a view of the leads to the camera 10. The processor determines the distance $D_B$ as the distance between the reference edge 302 and the image of the object 330 as indicated by the optical path 320. Using the angle θ 340 defined by optical path 310 and a plane parallel to the reticle plane intersecting object 330, the processor determines the distance Z 350 of the object 330 above the reticle plane. FIG. 7 shows an example calculation of θ during a calibration of the system. The processor calculates the Z dimension using the equation:

$$Z = D_S \tan(45° - \theta/2) - (D_B - D_S)\tan\theta$$

where:
- $D_S$=distance from the reference edge to the side view image of the object;
- $D_B$=distance from the reference edge to the bottom view image of the object;
- θ=angle formed by the ray emanating from the object reflected by the optical element and received by the camera and the plane intersecting the object parallel to the reticle plane; and
- Z=distance along the Z axis from the reticle plane to the object.

Figure 3B:
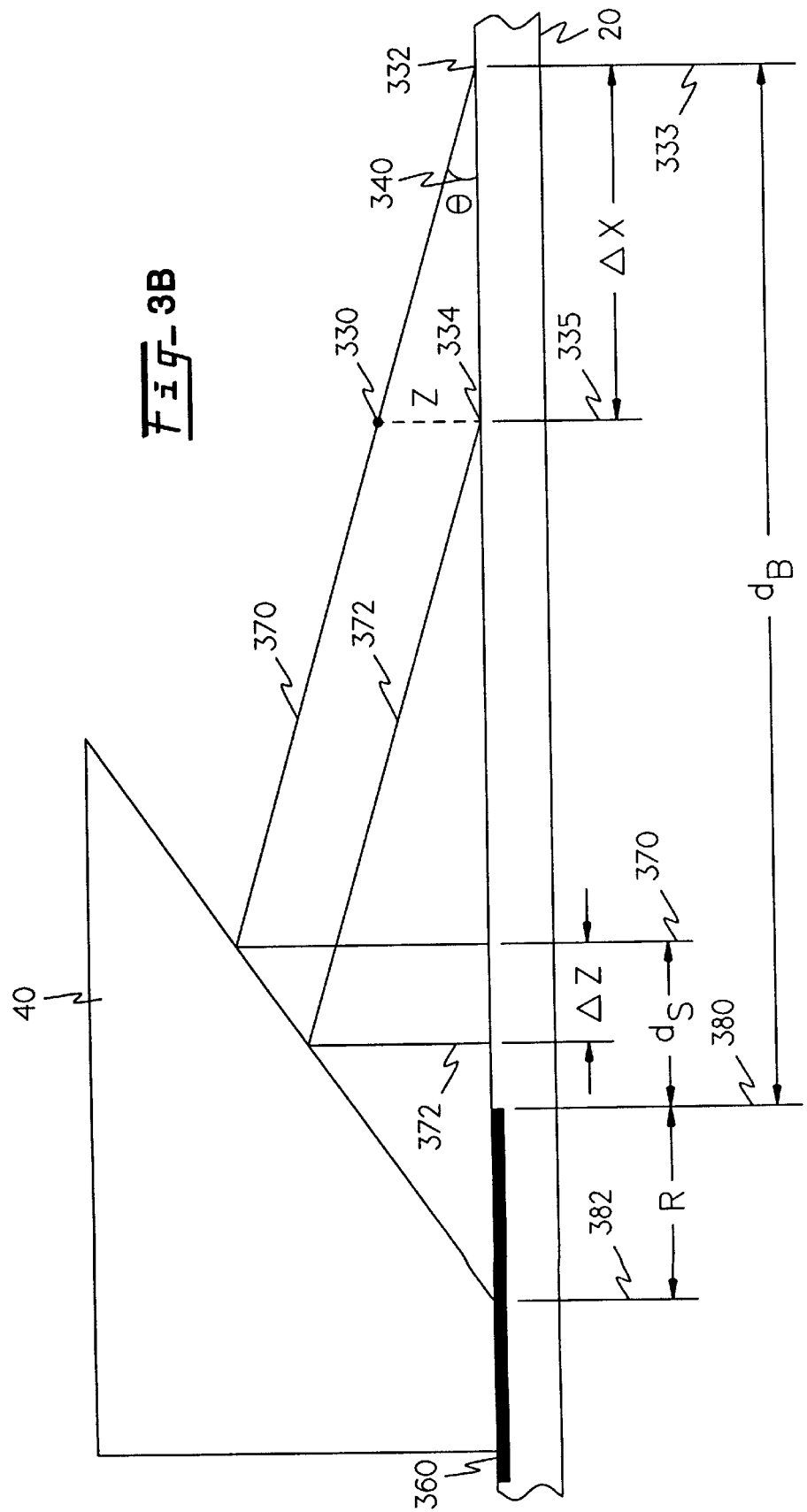
FIG. 3B shows an alternate method of the invention used to locate an object in three dimensions.

FIG. 3B shows an alternate method of the invention used to locate an object in three dimensions. In this method, the processor 14 begins by locating a reference line 360 inscribed on the reticle 20. The processor determines an angle θ 340 that is dependent upon the angle of the face 312 of the optical element 40 to the plane of the reticle 20. The angle θ 340 is determined by using two points 332 and 334. The processor determines a distance between points 332 and 334 by measuring the distance between two rays 333 and 335 that are parallel to the axis of the camera and extending downward from points 332 and 334. The processor then examines the side view for the corresponding rays 370 and 372 received by the camera from the optical element 40. The distance between these two rays 370 and 372 in the side view is measured as Δ Z. θ is determined using the following equation:

$$\theta = \text{ARCTAN}\left(\frac{\Delta Z}{\Delta X}\right).$$

The process then determines an offset R where R is a measure of a distance from the intersection 382 of the face 312 of the optical element and the plane of the reticle 20 and the edge of the reference line 360. The offset R is determined according to the following equation:

$$R = \frac{(d_B - d_s)\tan\theta}{\tan(45° - \theta/2)} - d_s$$

where:
- $d_S$=distance from a reference edge to the side view image of the object, which is the distance from rays 380 and 370;
- $d_B$=distance from a reference edge to the bottom view image of the object, which is the distance between rays 380 and 333;
- θ=angle formed by the ray emanating from the object reflected by the fixed optical element and received by the camera and the plane intersecting the object parallel to the reticle plane; and
- R=offset of reference line 360 and the intersection 382 between a reflective face of the optical element 40 and the transparent reticle 20.

The processor then determines the height Z of an object above the upper surface of the reticle 20, using the following equation:

$$Z = (d_S + R)\tan(45° - \theta/2) - (d_B - d_S)\tan\theta$$

where Z equals the distance along the Z axis from the reticle plane to the object.

Figure 5:
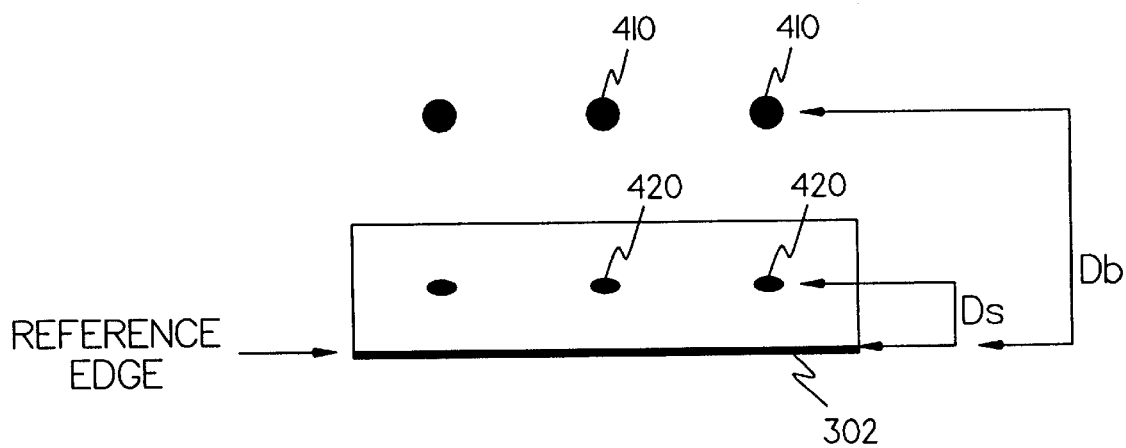
FIG. 5 shows a method of the invention for determination of $D_S$ and $D_B$.

In one embodiment of the invention, the system is calibrated by placing a pattern of calibration dots of known spacing and size on the reticle plane. FIG. 4 shows one embodiment of a calibration dot pattern as viewed by the camera 10 with four side optical elements, fewer or more side optical elements may also be used. The camera receives an image including a bottom view and four side views from the optical elements located on the reticle plane. The calibration dots appear as direct images 410 and reflected images 420. FIG. 5 shows the relationship between the direct image 410, the reflected image 420 and the reference edge 302 and the values of $D_S$ and $D_B$.

FIG. 6 shows a method of the invention used to calibrate the system using the reticle mask 400. The method begins at step 600 by finding the calibration dots. The processor finds a location and size of each dot visible directly from the bottom view and stores these results in memory. By comparing these results to known values stored in memory, the processor calculates the missing state values for the bottom calibration in steps 610 and 620. For example, in step 610 the processor determines camera distortion and roll angle and in step 620 the processor measures pixel width and height. These state values include pixel width and pixel height, pixel aspect ratio, optics distortion, and camera orientation with respect to the dot pattern. The processor then stores these results in memory. These results provide conversion factors for use during analysis to convert pixel values to world values.

The process flows to step 630 where the processor finds calibration dots visible in side views and reference edges. From these values, the processor determines the side view angles of the optical elements 40 in step 640 as shown in FIG. 7. The processor begins by finding the missing state values for each side mirror calibration from the data. These include the position of the mirror to the reticle plane. The state values are stored in memory.

FIG. 7 shows how the system determines angle θ 710 for the optical element 720 using $D_S$ and $D_B$. The system locates a reference edge 730 and uses a reflected image 740 of the object 750 to determine a distance $D_S$ 760. $D_B$ is determined by the distance from the reference edge 730 and the object 750. The angle calculation for angle θ 710 may be determined by the following calculation:

$$\theta = \text{ArcSin}\left[\frac{D_S}{D_B}\right]$$

where:

$D_S$=distance from a reference edge to the side view image of the object, which is the distance from rays 380 and 370;

$D_B$=distance from a reference edge to the bottom view image of the object, which is the distance between rays 380 and 333; and θ=angle formed by the ray emanating from the object reflected by the fixed optical element and received by the camera and the plane intersecting the object parallel to the reticle plane.

Once angle θ is known, the inspection system may use these known values to determine the three dimensional location of an object in space.

FIG. 8 shows one embodiment of a method of the inspection system of the invention to determine a three dimensional position of an object in space. The method begins in step 800 by finding an object from the bottom view. Using a search method, the processor determines coordinates for the object. In one embodiment, the processor may employ a subpixel method as shown below in FIGS. 10A–10D to find a repeatable position. The method then proceeds to step 810 to find the object in a side view. The processor determines a subpixel location for the object in the same manner as for the bottom view. The processor finds a reference edge to a subpixel location in step 820, and then computes the observed values for $D_S$ and $D_B$ in step 830. From these known values, the processor may determine the x, y and z positions of the object in step 840.

FIGS. 9A, 9B, 9C and 9D show alternate embodiments of the part holder and optical elements of the invention. In FIG. 9A, a pedestal 910 is attached to the central portion of the reticle 920. A part 900 may be received on the pedestal 910 for analysis. In FIG. 9B, a vacuum holder 950 is used to suspend a part 900 above the top surface of the reticle 920. The vacuum holder 950 suspends the part 900 substantially parallel to the face of the reticle 920. FIG. 9C shows a vacuum holder 950 suspending a part 900 above a reticle 920 where a central portion 922 of the reticle has been cut out. The central portion 922 of the reticle 920 has been cut out so that an inward face 942 of a prism 940 is substantially in line with the cut out portion of the reticle 920. FIG. 9D shows a configuration similar to that shown in FIG. 9C, except that a mirror 952 is used in place of the prism 940.

Figure 10A:
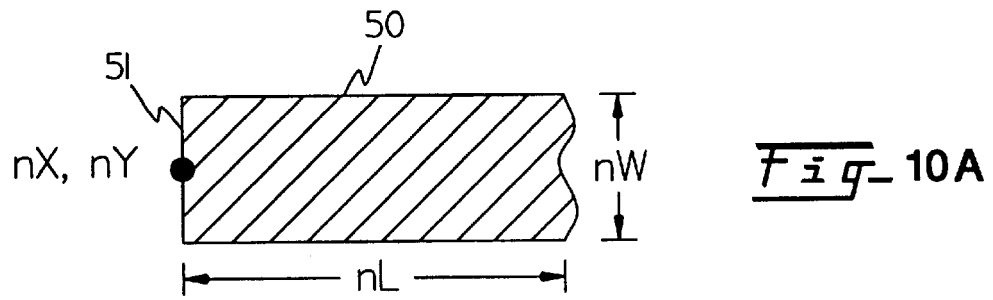
FIGS. 10A, 10B, 10C and 10D show one embodiment of the subpixel lead dimension measurement method.

Refer now to FIGS. 10A–10D which show one embodiment of the subpixel lead dimension measurement method. The processor begins with known parameters determined from the bottom view to find an ideal location center for a lead 50 having a lead tip 51. Depending on the size of a part and other parameters such as lighting conditions, the ideal location center of the lead tip 51 may vary. The processor defines a region of interest, 11×19 pixels for example, around the ideal location center, shown in FIG. 10A as the coordinates nX, nY. For example the camera is a CCD camera that contains 1024×1024 pixels with a pixel representing approximately 1.6 thousandths of an inch of the lead. Other optical systems and camera types may be used without deviating from the spirit and scope of the invention. The size of the region of interest is chosen such that only one lead is contained in the region so that no other adjacent lead is contained in that region of interest. Using nW, an expected width in pixels, and nL, an expected length available of the lead 50 up to the body of the part, an expected lead dimensions are found as shown in FIG. 10A. Within the region of interest, a processor finds a lead tip 51 by moving from the outside edge opposite the lead tip 51 toward the lead tip 51 one pixel at a time. The processor determines the pixel having the maximum gradient to be the edge of the lead tip dT. The gradient for each pixel is found by subtracting a gray scale value of the pixel from the gray scale value of the next pixel. To reduce the possible effects of noise, the processor may proceed by averaging groups of three or more pixels, as an example, rather than using individual pixels. When the lead tip 51 is found, the processor determines the two lead tip edges positions, $dS_1$ and $dS_2$ by moving five pixels, for example, into the lead along an axis parallel to the lead as defined by the ideal part. Then the method moves toward each of the side edges along a line perpendicular to the lead until a maximum gradient is found along the line. The pixel with the maximum gradient $dS_1$ and $dS_2$ are defined as the side positions.

Figure 10B:
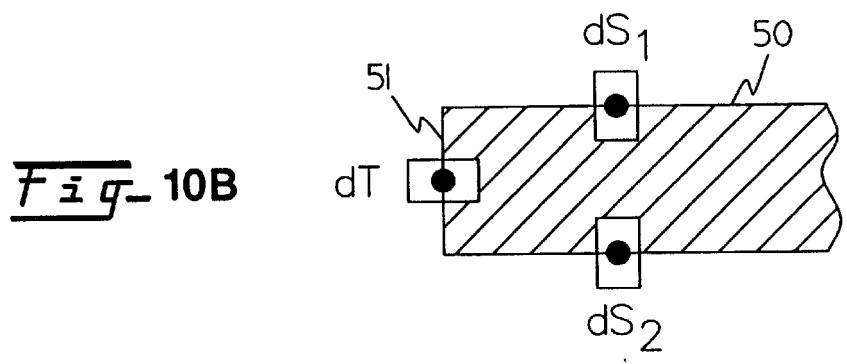

The processor then performs a subpixel operation as shown in FIG. 10B to find a more accurate seed position for a second subpixel operation. The processor defines a small 3×5 box around each position dT, $dS_1$ and $dS_2$. The subpixel operation begins on dT by averaging the three pixels in each column moving left to right and finding a more repeatable seed position dT. Likewise, more accurate seed positions $dS_1$ and $dS_2$ are found for the side locations moving from the non-lead edge into the lead while averaging the pixels in each row.

Figure 10C:
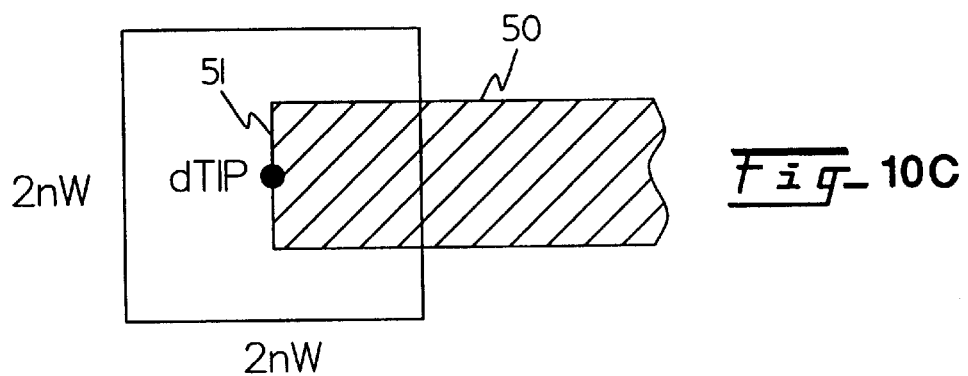

Once these new seed pixels have been determined, the processor determines tip position using the new seed point dTip and defining a large subpixel box of size 2nW×2nW where the tip point is centered left to right on dT, and centered top to bottom on $(dS_1$ and $dS_2)/2$ as shown in FIG. 10C. Once again, the processor moves from left to right from a non-lead edge into the lead while averaging the pixels in each column to find dTip as the tip position. By using a larger box having more pixels, a more repeatable result is obtained.

Figure 10D:
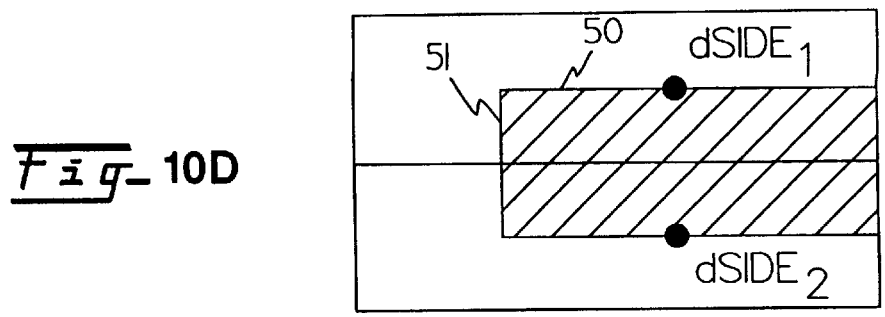

Likewise, as shown in FIG. 10D, the side positions are found using the seed positions $dS_1$ and $dS_2$ with a subpixel box of dimensions nL×nW. For one box the seed position is $dS_1$ and (dTip+nL/3). For the second box the seed position is $dS_2$ and (dTip+nL/3). The processor moves towards the lead averaging the pixels in each row, and using the subpixel process shown below, determines a subpixel location of the lead edges as $dSide_1$ and $dSide_2$. The width of the lead is then computed as $dSide_1-dSide_2$.

One example of subpixel edge detection implemented in the C language is shown below.

```
void IML_FindHorzEdge ( int nXseed,int nYseed,
                        int nWidth,int nLength,
                        double * dEdge)
{
        int nXstart = nXseed - (nLength - 1) /2;
        int nYstart = nYseed - (nWidth - 1) /2;
        int nXstop = nXstart + nLength;
        int nYstop = nYstart + nWidth;
        int nArray [MAX_LENGTH];
        double d1, d2, d3;
        double dL '2 nLength;
        double dM1 = 0.0;
        double dM2 = 0.0;
        double dM3 = 0.0;
        double dM3 = 0.0;
        double dM11;
        for (int x=nXstart;x<nXstop;x++)
        {
                d1 = 0.0;
                nArray ]x-nXstart] = 0;
                for (int xYstart;y<nYstop;y++)
                {
                        nArray ]n-nXstart] += GET_PIXEL (x,y);
                }
                d1 = nArray [x-nXstart];
                d2 = d1 + d1;
                d3 = d2 + d1;
                dM1 += d1;
                dM2 += d2;
                dM3 += d3;
        }
        dM1 /= dL;
        dM2 /= dL;
        dM3 /= dL;
        dM11 = dM1 + dM1;
        double dS1 = dM3 - dM1 * (3.0 *dM2-2.0*dM11);
        double dS2 = (dM2 - dM11) * sprt(fabs (dM2-dM11));
        if (dS2 == 0.0) dS2 - 1.0;
        double dS3 = dS1 / dS2;
        double dP = 0.5-dS3/(2.0*sqrt(4.0 + dS3 * dS3));
        double dE = dP*dL + 0.5;
        if (nArray [0] > nArray[nLength - 1])
                *dEdge = (double)nXseed - (double) (nLength+1)/2.0
+ dE;
            else
                *dEdge = (double)nXseed + (double) (nLength+1)/2.0 -
dE;
```

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An apparatus for three dimensional inspection of electronic leads, the apparatus comprising:

a) a transparent reticle having a top surface, wherein the transparent reticle receives a part having electronic leads for inspection on a central portion of the top surface;

b) a fixed optical element attached to the top surface of the transparent reticle, wherein the fixed optical element is positioned to reflect a side view of the part through the transparent reticle;

c) a camera located below the transparent reticle positioned to receive an image, including a bottom view of the part through the transparent reticle and the side view of the part from the fixed optical element, wherein the camera has an image data output representative of the bottom view and the side view; and d) a processor connected to receive the image data output, wherein the processor performs a three dimensional analysis on the image data output to inspect the electronic leads, wherein the processor has an electronic lead inspection result.

2. The apparatus of claim 1 wherein the apparatus employs a reticle mask for calibration, wherein the reticle mask further comprises a calibration dot pattern.

3. The apparatus of claim 1 further comprising four fixed optical elements attached around the central portion of the transparent reticle to provide four side views of the part to the camera.

4. The apparatus of claim 1 wherein the fixed optical element further comprises a prism.

5. The apparatus of claim 1 wherein the fixed optical element further comprises a mirror.

6. The apparatus of claim 1 wherein data from the image data output from the camera is stored in a memory.

7. The apparatus of claim 1 wherein the processor determines a height above the transparent reticle of an object according to the following equation:

$$Z=D_S\tan(45°-\theta b/2)-(D_B-D_S)\tan\theta$$

where:

$D_S$=distance from a reference edge to the side view image of the object;

$D_B$=distance from a reference edge to the bottom view image of the object;

$\theta$=angle formed by a ray emanating from the object reflected by the fixed optical element and received by the camera and a plane intersecting the object parallel to a transparent reticle plane; and Z=distance along the Z axis from the transparent reticle plane to the object.

8. The apparatus of claim 7 wherein an intersection of a reflective face of the fixed optical element and the transparent reticle is the reference edge.

9. The apparatus of claim 1 wherein the processor determines a height above the transparent reticle of an object according to the following equation:

$$Z=(d_S+R)\tan(45°-\theta/2)-(d_B-d_S)\tan\theta$$

where:

$d_S$=distance from a reference edge to the side view image of the object;

$d_B$=distance from a reference edge to the bottom view image of the object;

θ=angle formed by a ray emanating from the object reflected by the fixed optical element and received by the camera and a plane intersecting the object parallel to a transparent reticle plane;

R=offset of the reference edge and the intersection between a reflective face of the fixed optical element and the transparent reticle; and Z=distance along the Z axis from the transparent reticle plane to the object.

10. The apparatus of claim 9 wherein the processor determines θ and an offset R according to the following equations:

$$\theta = \text{ARCTAN}\left(\frac{\Delta Z}{\Delta X}\right)$$

$$R = \frac{(d_B - d_s)\tan\theta}{\tan(45° - \theta/2)} - d_s$$

where Δ x=distance between two objects on the bottom view; and

Δ z=corresponding distance between the two objects on the side view.

11. The apparatus of claim 1 wherein the camera is adjusted to provide a depth of focus encompassing an optical path from the part to the camera and an optical path from the part to the fixed optical element to the camera.

12. The apparatus of claim 1 wherein a vacuum holder suspends the part above the transparent reticle.

13. The apparatus of claim 12 wherein the central portion of the transparent reticle is cut out.

14. The apparatus of claim 1 further comprising a pedestal mounted on the central portion of the transparent reticle to receive the part.

15. The apparatus of claim 1 wherein the camera is positioned so that the axis of the camera is substantially perpendicular to a surface of the transparent reticle.

16. A method for three dimensional inspection of electronic leads from a single image, the method comprising the steps of:

a) providing a transparent reticle having a top surface;

b) placing a part having electronic leads for inspection on a central portion of the top surface of the transparent reticle;

c) providing fixed optical elements for providing a side perspective of the part;

d) providing a camera located beneath the transparent reticle to receive an image of the part and the side perspective provided by the fixed optical elements wherein the camera provides image data; and e) processing the image data with a computer to provide a three dimensional analysis of the part.

17. The method of claim 16 further comprising the step of calibrating the computer using a reticle mask.

18. The method of claim 17 wherein calibrating the computer further comprises calibration of a bottom view by:

a) locating calibration dots on the reticle mask that are visible directly from the bottom view;

b) determining a location and size of a dot;

c) storing the location and size of the dot in memory;

d) determining state values for calibration of the bottom view by comparing the location and size of the dot with known values; and e) storing the state values in memory.

19. The method of claim 18 wherein calibrating the computer further comprises calibration of a side view by:

a) locating the calibration dots that are visible in each one of the fixed optical elements;

b) locating a reference edge;

c) calculating a distance from the reference edge to the dot in the side view and the bottom view;

d) determining state values for the fixed optical elements from known values; and e) storing the state values in memory.

20. A method for providing three dimensional inspection of an object having electronic leads from a single image, the method comprising the steps of:

a) waiting for an inspection signal;

b) acquiring an image of the object including a bottom view and a side view;

c) processing the image to find a rotation, x placement and y placement of the object;

d) locating the electronic leads of the object in the bottom view;

e) locating the electronic leads of the object in the side view;

f) determining a reference point for the electronic leads;

g) converting pixel values to world values;

h) converting world values to part values;

i) converting part values to measurement values, wherein the measurement values are determined by comparing the part values to predetermined part values; and j) providing a part result based on the measurement values and predetermined tolerance values.

21. The method of claim 20 wherein the part result comprises a result selected from the group of: a pass result, a fail result and a rework result.

22. The method of claim 20 wherein the predetermined tolerance values further comprise pass tolerance values and fail tolerance values.

23. The method of claim 22 wherein the part result comprises a pass result if the measurement values are less than or equal to the pass tolerance values, a fail result if the measurement values exceed the fail tolerance values and a rework result otherwise.

24. The method of claim 20 wherein the image is stored in memory.

25. The method of claim 20 wherein the object is removed after the image is acquired and a next object placed while the part result is calculated.

26. The method of claim 20 wherein the steps of locating the electronic leads of the object in the bottom view and locating the electronic leads of the object in the side view further comprises the steps of:

(a) processing an image of a lead wherein the image comprises an image of a lead tip to generally locate a region of the image that contains the lead tip;

(b) defining a region of interest that contains the lead tip including a lead tip edge and lead tip sides;

(c) performing a subpixel edge detection over the region of interest to find a location of a center of the lead tip.

27. The method of claim 26 wherein the region of interest is sized to include only an image of one full lead.

* * * * *

UNITED STATES PATENT AND TRADEMARK OFFICE
CERTIFICATE OF CORRECTION

PATENT NO. : 6,055,054
DATED : April 25, 2000
INVENTOR(S) : Beaty et al.

It is certified that error appears in the above-identified patent and that said Letters Patent is hereby corrected as shown below:

In the Abstract

Delete the word "imagining" and replace with the word -- imaging --.

In the References Cited :

Delete the reference "5,812,268  9/1998  Svetkoff et al.." and replace with -- 5,812,268  9/1998  Jackson et al.. --.

Insert the missing reference -- 5,812,269  9/1998  Svetkoff et al.. .--.

Column 2, line 39, delete the word "word" and replace it with -- world --.

Column 6, line 29, delete the equation "$\theta$=ARCTAN".

Column 9, line 35, delete the "'2" and replace it with -- = --.

Column 9, line 42, delete the "]" and replace it with -- [ --.

Column 9, line 43, delete the "int xYstart;" and replace it with -- int y=nYstart; --.

Column 9, line 44, delete the "]n" and replace it with -- [x --.

Column 9, line 56, delete the word "sprt" and replace it with -- sqrt --.

Column 10, line 49, delete the "$\theta$b/2" and replace it with -- $\theta$/2 --.

UNITED STATES PATENT AND TRADEMARK OFFICE
CERTIFICATE OF CORRECTION

PATENT NO. : 6,055,054
DATED : April 25, 2000
INVENTOR(S) : Beaty et al.

It is certified that error appears in the above-identified patent and that said Letters Patent is hereby corrected as shown below:

Column 11, line 27, delete the "$\Delta$ x=distance" and replace it with -- $\Delta$ X=distance --.

Column 11, line 29, delete the "$\Delta$ z=corresponding" and replace it with -- $\Delta$ Z=corresponding --.

Signed and Sealed this

Seventeenth Day of April, 2001

*Attest:*

NICHOLAS P. GODICI

*Attesting Officer*    *Acting Director of the United States Patent and Trademark Office*